United States Patent [19]

Stephenson et al.

[11] 4,118,499

[45] Oct. 3, 1978

[54] ANTI-ANXIETY AND ANTI-PARKINSONIAN 1-AMINOALKYL-2-ENDO-CHLORO-7,7-DIMETHYLNORBORNANES

[75] Inventors: Leslie Stephenson, London; Colin Smith, New Malden, both of England

[73] Assignee: Glaxo Laboratories Limited, Greenford, England

[21] Appl. No.: 730,980

[22] Filed: Oct. 8, 1976

[30] Foreign Application Priority Data

Oct. 15, 1975 [GB] United Kingdom ............... 42280/75
Oct. 15, 1975 [GB] United Kingdom ............... 42278/75

[51] Int. Cl.[2] ................... A61K 31/445; C07D 211/14

[52] U.S. Cl. ................................ 424/267; 260/239 A; 260/239 B; 260/293.56; 260/326.5 C; 260/326.8; 260/563 P; 424/244; 424/274; 424/325

[58] Field of Search ............ 260/239 A, 239 B, 326.8, 260/293.56, 563 P, 239 AR; 424/267, 274, 325, 244

[56] References Cited

U.S. PATENT DOCUMENTS

| | | | |
|---|---|---|---|
| 2,843,587 | 7/1958 | De Benneville | 260/247 |
| 3,483,254 | 12/1969 | Shen et al. | 260/563 P |

OTHER PUBLICATIONS

Index Chemicus, vol. 34, 118103 (1969). [Minardi, G. et al., Annali di Chimica, vol. 59 (#4), 335–349 (1969). ]

Migrdichian, V., Organic Synthesis, Reinhold Publishing Corp., NY, 1957, vol. I, p. 496 and vol. II., pp. 1427–1428.

Theilheimer, W., Synthetic Methods of Organic Chemistry, Interscience, NY, 1959, vol. 13, p. 66.

Fieser, L. F. and Fieser, M., Advanced Organic Chemistry, Reinhold Publishing Corp., NY, 1961, p. 495.

Smith, P. A. S., Chemistry of Open-Chain Organic Nitrogen Compounds, vol. I, W. A. Benjamin, NY, 1965, p. 25.

House, H. O., Modern Synthetic Reactions, 2nd Edition, W. A. Benjamin, Menlo Park, Cal., 1972, pp. 18 and 72.

Chemical Abstracts, 82:16403m (1975) [German Offen. 2,410,492, May, p., 9/26/74].

*Primary Examiner*—Henry R. Jiles
*Assistant Examiner*—Richard A. Schwartz
*Attorney, Agent, or Firm*—Bacon & Thomas

[57] ABSTRACT

1-Aminoethyl, 1-aminopropyl and 1-aminobutyl derivatives of 7,7-dimethylnorbornane are described. The amino groups are optionally substituted, for example by alkyl groups, or may be saturated heterocyclic amino groups. The alkylene group at the 1-position can also be substituted, and the 2-position can be substituted by chlorine. The compounds have CNS activity.

17 Claims, No Drawings

ANTI-ANXIETY AND ANTI-PARKINSONIAN 1-AMINOALKYL-2-ENDO-CHLORO-7,7-DIMETHYLNORBORNANES

This invention relates to new derivatives of 7,7-dimethylnorbornane (i.e. 7,7-dimethyl-[2.2.1]-bicycloheptane).

1-Aminoethyl, 1-aminopropyl- and 1-aminobutyl-7,7-dimethyl-norbornane and the derivatives thereof described below are new compounds and we have found that compounds in this series possess interesting central nervous system activity.

Thus in one aspect the invention provides 7,7-dimethyl-[2.2.2]-bicycloheptanes of the formula:

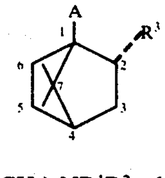

I wherein A is $-(CH_2)_nNR^1R^2$ where $n$ is 2, 3 or 4 (i.e. $-{}^{10}CH_2{}^{11}CH_2NR^1R^2$, $-{}^{10}CH_2{}^{11}CH_2{}^{12}CH_2-NR^1R^2$ or $-{}^{10}CH_2{}^{11}CH_2{}^{11}CH_2{}^{12}CH_2{}^{13}CH_2NR^1R^2$); $R^1$ and $R^2$, which may be the same or different, are hydrogen atoms or $C_{1-6}$ alkyl or $C_{2-6}$ alkenyl groups or, together with intervening nitrogen atom, represent a 4–7 membered saturated heterocyclic ring which is unsubstituted or substituted by a $C_{1-6}$alkyl group; and $R^3$ is a hydrogen or chlorine atom in the endo configuration; which compounds may optionally be additionally substituted by a $C_{1-4}$ alkyl group at any position in the alkylene chain of A or by an oxo or hydroxy group at the $\beta$-position of the alkylene chain of A relative to the nitrogen atom (i.e. at the 10-position when $n$ is 2, at the 11-position when $n$ is 3, or at the 12-position when $n$ is 4); and the salts thereof. The compounds just defined will be referred to herein as compounds of formula I.

Tests we have carried out in mice (including anti-nicotine, anti-rage and maximal electroshock tests) have shown that compounds of formula I possess central nervous system activity. The results of these tests indicate that these compounds are of potential interest as anti-Parkinson and/or tranquillizing drugs. Our anti-nicotine test is based on the methods of Bianchi and Tomasi (Pharmacology, 1973 10, 226–237) and Aceto, Bentley & Dembinski (Brit. J. Pharmacology, 1969, 37, 104–111). Convulsions are induced in mice by the intravenous (iv) or intracerebral (ic) injection of nicotine, the end point of the test being taken as the tonic extensor convulsion in the iv tests and the clonic convulsion in the ic tests. The anti-rage test used was that of Tedeschi et al (J. Pharmac. Exp. Ther. 125, 28–34), and the maximal electroshock test that of Swinyard et al (J. Pharmac. Exp. Ther. 106, 319–330).

The invention thus also includes pharmaceutical (including veterinary) compositions comprising a compound in accordance with the invention or a physiologically acceptable salt thereof together with a pharmaceutical carrier or excipient.

In the compounds of the invention $R^1$ and $R^2$ may for example be $C_{1-4}$ alkyl or $C_{2-4}$ alkenyl groups such as methyl, ethyl, n-propyl, n-butyl and allyl. When $R^1$ and $R^2$ together with the intervening nitrogen atom represent a heterocyclic ring, the group preferably has 5 or 6 ring members and may for example be a piperidino or pyrrolidino group; such groups may be substituted by one or more $C_{1-6}$alkyl (e.g. methyl) groups. Examples of alkyl groups which may be present on the alkylene chain of A are methyl, ethyl, n-propyl and n-butyl.

In general, the preferred compounds are those in which both $R^1$ and $R^2$ are hydrogen atoms, and also those in which the alkylene chain of A is unsubstituted. Compounds in which $n$ is 3 (i.e. aminopropyl compounds) are also generally preferred, as are those in which $R^3$ is a chlorine atom.

When $-NR^1R^2$ represents a substituted amino group it is preferably a monomethylamino group or (particularly when $R^3$ is a chlorine atom) a dimethylamino group. When $-NR^1R^2$ represents a heterocyclic amino group the ring preferably has 5 or 6 members, and $R^3$ is preferably a chlorine atom in such compounds. When the alkylene chain of A is substituted by an alkyl group the substituent is preferably a methyl group in the $\alpha$- or $\beta$-position relative to the nitrogen atom.

Specific compounds which are preferred on account of the activity they have shown in our tests are:

(1) 1-(2-aminoethyl)-7,7-dimethylnorbornane;

(2) 1-(2-aminoethyl)-2-endo-chloro-7,7-dimethylnorbornane;

(3) 1-(2-methylaminoethyl)-7,7-dimethylnorbornane;

(4) 1-(2-dimethylaminoethyl)-7,7-dimethylnorbornane;

(5) 1-(2-dimethylaminoethyl)-2-endo-chloro-7,7-dimethylnorbornane;

(6) 1-(2-pyrrolidinoethyl)-2-endo-chloro-7,7-dimethylnorbornane;

(7) 1-(2-piperidinoethyl)-2-endo-chloro-7,7-dimethylnorbornane;

(8) 1-(2-amino-n-propyl)-7,7-dimethylnorbornane;

(9) 1-(2-amino-n-propyl)-2-endo-chloro-7,7-dimethylnorbornane;

(10) 1-(1-oxo-2-dimethylaminoethyl)-7,7-dimethylnorbornane;

(11) 1-(3-amino-n-propyl)-7,7-dimethylnorbornane;

(12) 1-(3-amino-n-propyl) -2-endo-chloro-7,7-dimethylnorbornane;

(13) 1-(3-methylamino-n-propyl)-7,7-dimethylnorbornane;

(14) 1-(3-methylamino-n-propyl)-2-endo-chloro-7,7-dimethylnorbornane;

(15) 1-(3-dimethylamino-n-propyl)-2-endo-chloro-7,7-dimethylnorbornane;

(16) 1-(2-oxo-3-methylamino-n-propyl)-2-endo-chloro-7,7-dimethylnorbornane;

(17) 1-(2-hydroxy-3-amino-n-propyl)-7,7-dimethylnorbornane;

(18) 1-(2-hydroxy-3-amino-n-propyl)-2-endo-chloro-7,7-dimethylnorbornane;

(19) 1-(4-amino-n-butyl)-7,7-dimethylnorbornane;

(20) 1-(4-methylamino-n-butyl)-7,7-dimethylnorbornane;

(21) 1-(2-pyrrolidinoethyl)-7,7-dimethylnorbornane;

(22) 1-(2-piperidinoethyl)-7,7-dimethylnorbornane; and

(23) 1-(2-hexamethyleneimino)-7,7-dimethylnorbornane.

These compounds may be in the form of their salts, in particular hydrochlorides.

Examples of physiologically acceptable acid addition salts which are included in the invention are hydrochlorides, hydrobromides, phosphates, sulphates, p-toluene sulphonates, methane sulphonates, citrates, tartrates, acetates, ascorbates, lactates, maleates and succinates.

The compounds of the invention may be formulated for administration with one or more conventional carriers or excipients, together if desired with other medicinal agents, in a form suitable for oral, rectal or parenteral administration. If desired, the compositions may be formulated to provide delayed or sustained release of the active compound.

Thus for example the compositions may be presented in the form of tablets, capsules, suppositories and aqueous or oily solutions for injection, e.g. in ampoules. The compositions are preferably presented in dosage unit form, the units for example being formulated to provide 10 to 500 mg of the active compound per day (for the average adult having a body weight of 70kg). These doses may of course be varied for children or animals according to weight.

The compounds of the invention which are unsubstituted at the α-position in relation to the nitrogen atom are conveniently prepared by reduction of the corresponding carbonamide, i.e. a compound of formula I wherein the 11-, 12- or 13-position, as appropriate, is substituted by an oxo group (compounds of formula I except in that A is the group $-(CH_2)_{n-1}CONR^1R^2$).

This reaction may for example be carried out with a hydride reagent capable of reducing amides to amines, such as lithium aluminium hydride or diborane, in an inert organic solvent, for example a hydrocarbon solvent such as benzene or toluene or an ether solvent such as diethyl ether or tetrahydrofuran. The reaction with lithium aluminium hydride is suitably carried out at the reflux temperature of the reaction mixture although lower temperatures may be used if desired. Reaction with diborane may for example be effected at temperatures of $-10°$ to $+30°$ C., conveniently at room temperature. The amine produced is conveniently isolated in the form of a salt, e.g. the hydrochloride.

The amides required as intermediates in the reaction are new compounds and they constitute a further embodiment of the invention.

The amides required for the reduction reaction may be prepared from the corresponding carboxylic acid, i.e. compounds of formula I wherein A is $-CH_2COOH$, $-C_2H_4COOH$ or $-C_3H_6COOH$ or such a group in which the alkylene chain is substituted by an alkyl group.

The amides may be prepared by reacting the acid itself or a reactive derivative thereof (e.g. an acid halide such as an acid chloride) with ammonia or an amine of the formula $HNR^1R^2$.

This reaction is desirably carried out at a low temperature (e.g. $-80°$ to $+10°$ C.) in the presence of an acid binding agent (e.g. a base, which is conveniently provided by an excess of the amine). The reaction conveniently carried out in a hydrocarbon solvent such as toluene or an ether solvent such as diethyl ether.

Where an acid halide is chosen for the reaction, it may be prepared by conventional techniques, e.g. by reacting the acid with thionyl chloride.

The amide preparation just described is a particularly suitable method of preparing amides of the formula I wherein A is $-CH_2CONR^1R^2$, $-C_2H_4CONR^1R^2$ or $-C_3H_6CONR^1R^2$, the alkylene groups being unsubstituted or substituted by a $C_{1-4}$ alkyl group.

As regards the carboxylic acids required as starting materials in the amide preparations, the compound in which A is $-CH_2COOH$ is known (i.e. 1-apocamphane acetic acid), as is its 2-chloro derivative. The compounds wherein A is $-C_2H_4COOH$ are for example conveniently prepared from a compound of formula I wherein A is $-C_2H_4OH$ (e.g. 1-(2-hydroxyethyl)-7,7-dimethylnorbornane) by first forming the corresponding 11-bromo compound, for example by refluxing with hydrobromic acid in the presence of a strong acid (e.g. sulphuric acid). The bromo compound may then be converted into the desired acid either by reaction with magnesium and carbon dioxide or by reaction with an alkali metal cyanide (e.g. KCN) followed by treatment with a strong base, e.g. an alkali metal hydroxide such as KOH.

The carboxylic acid starting materials in which A is $-C_3H_6COOH$ (or such a group substituted by alkyl) may for example be prepared by treating a corresponding bromoethyl compound with an alkali metal dialkylmalonate (e.g. sodium diethylmalonate) and then hydrolysing the product (e.g. with KOH). The dicarboxylic acid produced may then be decarboxylated (e.g. by heating at 170°-180° C.) to give the required intermediate.

The amides of formula I in which A is $-C_2H_4CONR^1R^2$ or $-C_3H_6CONR^1R^2$ may also be prepared by reaction of a β-keto diazo compound (i.e. a compound of formula I except in that A is $-CH_2COCHN_2$ or $-C_2H_4COCHN_2$) with ammonia or an amine of the formula $HNR^1R^2$ in the presence of silver nitrate. This reaction is preferably performed in aqueous dioxan solution at a moderate temperature (e.g. 60°-80° C.).

The β-keto diazo compounds required for this latter reaction (as well as those in which A is $-COCHN_2$) may themselves be prepared by reaction of an appropriate carboxylic acid halide (i.e. a compound of formula I in which A is $-COX$, $-CH_2COX$ or $-C_2H_4COX$ where X is halogen, e.g. chlorine) with diazomethane. This reaction is desirably carried out at low temperature (e.g. 0° C.) in an ether solvent (e.g. diethyl ether), using an excess of diazomethane. Acid halides used as a starting materials in this reaction may again be prepared by conventional techniques.

Compounds which are substituted at the β-position in relation to the nitrogen atom by an oxo or hydroxy group (i.e. 10-substituted compounds when A is $-C_2H_4NR^1R^2$, 11-substituted compounds when A is $-C_3H_6NR^1R^2$ or 12-substituted compounds when A is $-C_4H_8NR^1R^2$) may also be prepared from the β-keto diazo compounds just described.

The β-keto amines may for example be prepared by first converting the diazo compound into the corresponding halo compound (e.g. a compound of formula I wherein A is $-COCH_2Cl$, $-CH_2COCH_2Cl$ or $-C_2H_4COCH_2Cl$) and secondly reacting the halo compound with an amine of the formula $HNR^1R^2$. The first step of this reaction may be carried out by reacting the diazo compound with a hydrogen halide (e.g. HCl), e.g. at a low temperature (e.g. 0° C.) in an ether solvent. The second step may carried out generally as described above with regard to the preparation of amides from acid halides.

When a β-hydroxy compound is required, it may for example be prepared by subsequently reducing the β-keto amine, for example as described above for the reduction of amides to amines.

β-Hydroxy compounds wherein $-NR^1R^2$ is an unsubstituted amino group may be prepared by reducing the corresponding β-keto diazo compounds. The reduction may again be effected with lithium aluminium hydride or diborane, as described above. The diazo starting materials may be prepared as described above, and they have the formula $R^4COCHN_2$ where $R^4$ is the group of formula I given by removal of the terminal $—CH_2CH_2NR^1R^2$ group.

Compounds having a $C_{1-4}$ alkyl group at the β-position may be prepared by reacting an ester of the formula $R^4CH_2COOR^5$ (where $R^5$ is an alkyl group, e.g. ethyl, and $R^4$ is as just defined) firstly with N-cyclohexyl-N-iso-propylamino lithium and secondly with an alkyl halide (e.g. mthyl iodide) to give a compound of the formula

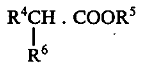

where $R^6$ is the alkyl group. This ester may then be converted to its parent acid, for example with boron tribromide; the acid may then be converted into the desired amino compound as described above, i.e. via the acid halide and amide. Alternatively, the ester

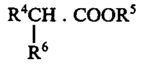

may be converted first into a hydroxyethyl, hydroxypropyl or hydroxybutyl compound (i.e.

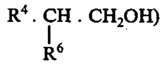

by reduction, for example with lithium aluminium hydride. This hydroxyalkyl compound may then be converted into the corresponding haloalkyl compound, for example by treatment with a hydrohalic acid; the desired amine may then be prepared from this haloalkyl compound by the method described generally below.

The compounds of the invention may also be prepared by reacting the corresponding haloalkyl compound with ammonia or an amine of the formula $HNR^1R^2$. This reaction may for example be carried out by refluxing the halo compound with the amine in a suitable solvent (e.g. the amine itself, a hydrocarbon such as toluene, or an alcohol) in the presence of an acid binding agent (e.g. potassium carbonate or an excess of the amine). This process is particularly suitable for the preparation of compounds which are either unsubstituted in the alkylene chain of A or which are substituted by an alkyl group at the β-position.

The halo compounds used in this preparation (e.g. the 2-bromoethyl compounds) are new.

Compounds in which the α-position is substituted by an alkyl group may be prepared by reductive amination of an appropriate ketone (i.e. a compound of the formula $R^4CH_2COR^7$, where $R^7$ is the alkyl group). This reaction may for example be performed by reacting the ketone with ammonia or an amine of the formula $HNR^1R^2$ either in the presence of hydrogen (under a pressure of for example 4 atmospheres) over a platinum oxide catalyst (e.g. Adams' catalyst), or in the presence of sodium cyanoborohydride. In the former method, the reaction solvent is suitably a mixture of acetic acid and ethanol, and in the latter method an alcohol such as methanol may be used. The starting materials for the reaction may be prepared from the acid $R^4CH_2COOH$ by reaction with an alkyl lithium.

Compounds in which $R^1$ is an alkyl (e.g. methyl) group and $R^2$ is a $C_{1-6}$ alkyl or alkenyl group may be prepared by alkylating the corresponding monosubstituted compound (i.e. $R^1 = H$); compounds in which $R^1$ is a methyl group may thus for example be prepred by reacting the corresponding monosubstituted compound with formaldehyde and formic acid. Similarly, the corresponding unsubstituted amines can be alkylated to form di-substituted amines.

The compounds of formula I in which $R^1$ and $R^2$ are both hydrogen and the α-position in relation to the nitrogen atom is unsubstituted may also be prepared by reducing the corresponding cyanoalkyl compound (i.e. compound of the formula $R^4CH_2CN$). The reduction may for example be effected with lithium aluminium hydride, using the above described reaction conditions.

The cyanoalkyl compounds required as starting materials in the latter reaction may for example be prepared from the corresponding hydroxyalkyl compound by: (1) reacting the hydroxyalkyl compound with a hydrocarbylsulphonyl halide (e.g. p-toluene-sulphonyl chloride or preferably methane sulphonyl chloride) in the presence of triethylamine, e.g. at about 0° C. in an ether solvent, and (2) treating the hydrocarbyl sulphonate produced with an alkali metal cyanide (e.g. NaCN) at elevated temperatures, in a solvent (e.g. dimethylformamide or dimethylsulphoxide).

The following examples illustrate the invention. Temperatures are in ° C. "t.l.c." refers to thin layer chromatography, carried out on silica.

EXAMPLES 1-6

Preparation of 7,7-dimethylnorborn-1-yl aminoketones

The aminoketones whose properties are summarised in Table 1 were prepared by the following general method.

The appropriate carboxylic acid and excess thionyl chloride were heated on a steam-bath and evaporated to an oil in vacuo. A solution of the oil in dry ether was added dropwise with stirring to an ice-cold solution of diazomethane (approximately 2 equivalents) in ether. The mixture was stirred at 0° for 2 hours and then hydrogen chloride was passed through the cooled solution for 1 hour. After standing at room temperature overnight the solution was poured onto ice/water and the ether layer separated. The aqueous layer was extracted again with ether and the etheral solutions combined. The extracts were washed with water, dilute sodium bicarbonate and water, dried ($MgSO_4$) and evaporated in vacuo to yield the crude α-chloroketone which was used without further purification.

A solution of the α-chloroketone and the appropriate amine (2.2 equivalents) in toluene were set aside for the periods shown in Table 1 at room temperature and filtered. The filtrate was evaporated in vacuo, dissolved in dry ether and cooled. A cold solution of hydrogen chloride in ether was added, the hydrochloride filtered and recrystallized from the given solvent.

TABLE 1

7,7-Dimethylnorborn-1-yl Aminoketones

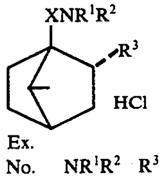

HCl

| Ex. No. | $NR^1R^2$ | $R^3$ | Reaction Time (h) | m.p. ° C | Recrystallisation Solvent | Empirical Formula | C Found | C Req. | H Found | H Req. | Cl Found | Cl Req. | N Found | N Req. |
|---|---|---|---|---|---|---|---|---|---|---|---|---|---|---|
| 1 | NHMe | H | 18 | 303–4 (d) | I.M.S. | $C_{12}H_{22}Cl$ NO | 62.2 | 62.2 | 9.4 | 9.6 | 15.2 | 15.3 | 6.3 | 6.0 |
| 2 | $NMe_2$ | H | 17 | 258–9 (d) | Ethyl Acetate/ Propan-2-OL | $C_{13}H_{24}Cl$ NO | 62.7 | 63.5 | 9.9 | 9.8 | 14.4 | 14.4 | 5.6 | 5.7 |
| 3 | $NMe_2$ | H | 18 | 232–4 | Propan-2-OL | $CH_{14}H_{26}Cl$ NO | 65.0 | 64.7 | 10.2 | 10.1 | 13.1 | 13.6 | 5.1 | 5.4 |
| 4 | $NMe_2$ | Cl | 18 | 200–2 | Methyl Acetate | $C_{14}H_{25}Cl_2NO$ | 57.2 | 57.1 | 8.8 | 8.6 | 24.1 | 24.1 | 4.4 | 4.8 |
| 5 | P | Cl | 18 | 238 (d) | Propan-2-OL | $C_{17}H_{29}Cl_2NO$ | 60.9 | 61.0 | 8.7 | 8.7 | 21.4 | 21.2 | 4.0 | 4.2 |
| 6 | NHMe | Cl | 1.5 | 245–7 (d) | Propan-2-OL | $C_{13}H_{23}Cl_2NO$ | 56.0 | 55.7 | 8.3 | 8.3 | 25.4 | 25.3 | 4.8 | 5.0 |

I.M.S. = industrial methylated spirits
P = piperidino
(d) = decomposition
X = $-COCH_2$ in Ex. 1 and 2, $-CH_2COCH_2$ in Ex. 3–6.

EXAMPLES 7–40

Preparation of 1-(alkylamino)-and 1-(hydroxyalkylamino)-7,7-dimethylnorbornanes The amines, whose properties are described in Table 2 were prepared by the following general method.

A solution of the appropriate aminoketone or carbonamide in tetrahydrofuran was carefully added to a stirred suspension of an excess of lithiium aluminium hydride in the same solvent and the resulting mixture refluxed until the reaction, as judged by thin-layer chromatography, was complete. The excess lithium aluminium hydride was destroyed by the careful addition of water and dilute sodium hydroxide solution. The mixture was stirred at room temperature for 0.5 hours and insoluble material removed by filtration. The filtrate was evaporated, extracted into ether, washed with water, dried ($MgSO_4$) and evaporated in vacuo. The residual crude amine was dissoled in ether and the hydrochloride precipitated by addition of an ethereal solution of hydrogen chloride. The hydrochloride was collected by filtration, recrystallised from the given solvent and dried.

TABLE 2

1-(Alkylamino)- and 1-(Hydroxyalkylamino)-7,7-Dimethylnorbornanes

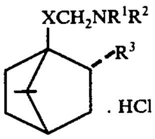

. HCl

| Ex. No. | X | $NR^1R^2$ | $R^3$ | m.p. ° C | Recrystallisation Solvent | Empirical Formula | C Found | C Req. | H Found | H Req. | Cl Found | Cl Req. | N Found | N Req. |
|---|---|---|---|---|---|---|---|---|---|---|---|---|---|---|
| 7 | $CH_2$ | $NH_2$ | H | >350 | Propan-2-ol | $C_{11}H_{22}ClN$ | 64.7 | 64.7 | 11.0 | 10.9 | 17.5 | 17.4 | 7.0 | 6.9 |
| 8 | $CH_2$ | NHMe | H | >350 | I.M.S. | $C_{12}H_{24}ClN$ | 66.2 | 66.2 | 11.15 | 11.1 | 16.3 | 16.3 | 6.0 | 6.4 |
| 9 | $CH_2$ | NHMe | Cl | 287(d) | I.M.S. | $C_{12}H_{23}Cl_2N$ | 57.6 | 57.1 | 9.4 | 9.2 | 27.9 | 28.1 | 5.2 | 5.55 |
| 10 | $CH_2$ | $NMe_2$ | H | 310(d) | I.M.S. | $C_{13}H_{26}ClN$ | 67.1 | 67.3 | 11.5 | 11.3 | 15.55 | 15.3 | 5.8 | 6.0 |
| 11 | $CH_2$ | $NMe_2$ | Cl | 236–8 | M.A. | $C_{13}H_{25}Cl_2N$ | 58.6 | 58.7 | 9.5 | 9.5 | 26.5 | 26.6 | 5.15 | 5.3 |
| 12 | $CH_2$ | P | H | 349(d) | I.M.S. | $C_{16}H_{30}ClN$ | 70.6 | 70.7 | 11.2 | 11.1 | 13.05 | 13.0 | 4.8 | 5.15 |
| 13 | $CH_2$ | P | Cl | 281(d) | Propan-2-ol | $C_{16}H_{29}Cl_2N$ | 62.6 | 62.7 | 9.3 | 9.5 | 23.6 | 23.2 | 4.2 | 4.6 |
| 14 | OH<br>CH | $NH_2$ | H | 332(d) | I.M.S. | $C_{11}H_{22}Cl$ NO | 60.0 | 60.1 | 10.3 | 10.1 | 15.95 | 16.1 | 6.4 | 6.6 |
| 15 | OH<br>CH | $NMe_2$ | H | 280(d) | Propan-2-ol | $C_{13}H_{26}Cl$ NO | 63.0 | 63.0 | 10.8 | 10.6 | 14.1 | 14.3 | 5.45 | 5.7 |
| 16 | OH<br>CH | P | H | 322–3(d) | Propan-2-ol | $C_{16}H_{30}Cl$ NO | 66.7 | 66.75 | 10.5 | 10.5 | 12.4 | 12.3 | 4.6 | 4.9 |
| 17 | $CH_3$<br>CH | $NMe_2$ | H | 251–5 | Propan-2-ol | $C_{14}H_{28}Cl$ N | 68.4 | 68.4 | 11.5 | 11.5 | 14.3 | 14.4 | 5.6 | 5.7 |
| 18 | $CH_2$ | 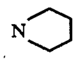 | H | 322(d) | Propan-2-ol | $C_{15}H_{28}Cl$ N | 69.8 | 69.9 | 10.9 | 10.95 | 13.9 | 13.75 | 5.35 | 5.4 |
| 19 | $CH_2$ | 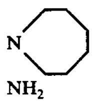 | 25-9-- 260(d) | Propan-2-ol | $C_{17}H_{31}Cl_2N$ | 63.5 | 63.7 | 9.8 | 9.8 | 22.0 | 22.1 | 4.4 | 4.4 | |
| 20 | $(CH_2)_2$ | $NH_2$ | H | 320–4(d) | I.M.S./ ether | $C_{12}H_{24}ClN$ | 66.4 | 66.1 | 11.4 | 11.1 | 16.25 | 16.3 | 6.4 | 6.4 |
| 21 | $(CH_2)_2$ | NHMe | H | 255(d) | I.M.S./ ether | $C_{13}H_{26}ClN$ | 67.6 | 67.4 | 11.05 | 11.3 | 15.6 | 15.3 | 5.8 | 6.0 |
| 22 | $(CH_2)_2$ | P | H | 324(d) | Propan-2-ol | $C_{17}H_{32}ClN$ | 71.3 | 71.4 | 11.0 | 11.3 | 12.4 | 12.4 | 4.9 | 4.9 |
| 23 | $CH_2$ .<br>CH(OH) | P | H | 292–4(d) | I.M.S. | $C_{17}H_{32}ClNO$ | 68.0 | 67.6 | 10.7 | 10.7 | 11.8 | 11.7 | 4.5 | 4.6 |
| 24 | $CH_2$ . | P | Cl | 222–4(d) | I.M.S. | $C_{17}H_{31}Cl_2NO$ | 60.8 | 60.7 | 9.5 | 9.3 | 21.4 | 21.1 | 4.05 | 4.2 |

TABLE 2-continued 1-(Alkylamino)- and 1-(Hydroxyalkylamino)-7,7-Dimethylnorbornanes

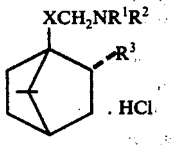

| Ex. No. | X | $NR^1R^2$ | $R^3$ | m.p. °C | Recrystallisation Solvent | Empirical Formula | C Found | C Req. | H Found | H Req. | Cl Found | Cl Req. | N Found | N Req. |
|---|---|---|---|---|---|---|---|---|---|---|---|---|---|---|
| 25 | $CH(OH)(CH_2)_2$ | $NH_2$ | Cl | 223–4(d) | E.A. | $C_{12}H_{23}Cl_2N.0.5H_2O$ | 55.6 | 55.1 | 9.1 | 9.3 | 27.4 | 27.15 | 5.4 | 5.4 |
| 26 | $(CH_2)_2$ | NHMe | Cl | 233(d) | M.A. | $C_{13}H_{25}Cl_2N$ | 58.4 | 58.65 | 9.3 | 9.5 | 26.4 | 26.6 | 5.5 | 5.3 |
| 27 | $(CH_2)_2$ | $NMe_2$ | Cl | 221–3 | I.M.S. | $C_{14}H_{27}Cl_2N$ | 59.7 | 59.95 | 9.8 | 9.7 | 25.1 | 25.3 | 4.5 | 5.0 |
| 28 | $(CH_2)_2$ | P | Cl | 273(d) | Propan-2-ol | $C_{17}H_{31}Cl_2N$ | 63.8 | 63.8 | 9.85 | 9.8 | 22.0 | 22.15 | 4.1 | 4.4 |
| 29 | $(CH_2)_3$ | $NH_2$ | H | 245–7(d) | Ethanol/Ether | $C_{13}H_{26}ClN.0.25H_2O$ | 66.1 | 65.95 | 11.4 | 11.3 | 14.7 | 15.0 | 6.0 | 5.9 |
| 30 | $(CH_2)_3$ | NHMe | H | 195–200(d) | E.A. | $C_{14}H_{28}ClN$ | 68.9 | 68.4 | 11.6 | 11.4 | 14.3 | 14.4 | 5.4 | 5.7 |
| 31 | $(CH_2)_3$ | $NMe_2$ | H | 233–5 | E.A. | $C_{15}H_{30}ClN$ | 68.9 | 69.3 | 11.8 | 11.6 | 13.55 | 13.6 | 4.9 | 5.4 |
| 32 | $(CH_2)_3$ | P | H | 308–9 | Propan-2-ol | $C_{18}H_{34}ClN$ | 72.0 | 72.2 | 11.5 | 11.4 | 11.9 | 11.8 | 4.5 | 4.7 |
| 33 | $(CH_2)_3$ | $NMe_2$ | Cl | 210–3(d) | Propan-2-ol/Ether | $C_{15}H_{29}Cl_2N$ | 61.4 | 61.2 | 10.1 | 9.9 | 24.2 | 24.1 | 4.6 | 4.8 |
| 34 | $(CH_2)_3$ | P | Cl | 270–5(d) | Propan-2-ol | $C_{18}H_{33}Cl_2N$ | 65.0 | 64.7 | 10.0 | 10.0 | 20.7 | 21.2 | 4.2 | 4.2 |
| 35 | $CH_2$ | $NEt_2$ | Cl | 142–3 | E.A. | $C_{15}H_{29}Cl_2N$ | 59.2 | 59.4 | 9.7 | 10.0 | 23.3 | 23.4 | 4.3 | 4.6 |
| 36 | $CH_2$ | 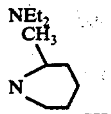 | Cl | 217–9 | Propan-2-ol | $C_{17}H_{31}Cl_2N$ | 64.0 | 63.7 | 10.1 | 9.8 | 22.25 | 22.1 | 4.2 | 4.4 |
| 37 | $CH_2$ | 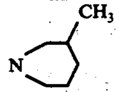 | Cl | 217 | Propan-2-ol/Ether | $C_{17}H_{31}Cl_2N$ | 63.6 | 63.7 | 9.7 | 9.8 | 22.4 | 22.1 | 4.6 | 4.4 |
| 38 | $CH_2$ | 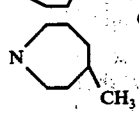 | Cl | 267(d) | Propan-2-ol/Ether | $C_{17}H_{31}Cl_2N$ | 64.4 | 63.7 | 9.7 | 9.8 | 22.3 | 22.1 | 4.1 | 4.4 |
| 39 | $CH_2$ | 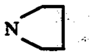 | Cl | 258–260(d) | Propan-2-ol | $C_{15}H_{27}Cl_2N$ | 61.5 | 61.6 | 9.4 | 9.3 | 24.1 | 24.3 | 4.6 | 4.8 |
| 40 | $CH_2$ | 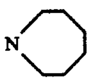 | H | 313–6(d) | Propan-2-ol | $C_{17}H_{32}Cl\ N$ | 71.3 | 71.4 | 11.1 | 11.3 | 12.2 | 12.4 | 4.8 | 4.9 |

P = piperidino;
M.A. = methyl acetate;
E.A. = ethyl acetate;
I.M.S. = industrial methylated spirits;
d = decomposition

EXAMPLE 41

1-(2-Aminoethyl)-2-endo-chloro-7,7-dimethylnorbornane hydrochloride

A solution of boron trifluoride diethyl etherate (26.8 ml) in tetrahydrofuran (20 ml) was added, over a period of 10 minutes, to a stirred suspension of sodium borohydride (5.40 g) in tetrahydrofuran (80 ml) at 0° and the resulting mixture stirred at room temperature for 1 hour. A solution of 1-(2-amino-2-oxo)ethyl-2-endo-chloro-7,7-dimethylnorbornane (2.58g) in tetrahydrofuran (20 ml) was added to the stirred mixture and stirring continued for a further 20 hours. The resulting mixture was carefully poured onto ice-water (200 ml) and concentrated hydrochloric acid (40 ml) added to the mixture. The mixture was then heated under reflux for 0.5 hours, cooled and partitioned between ether and water. The aqueous layer was separated, basified with 30% sodium hydroxide solution and extracted with ether. The combined extracts were washed with water, dried ($MgSO_4$) and evaporated in vacuo. The residual crude amine (0.89g) was dissolved in ether and the hydrochloride precipitated by the addition of an ethereal solution of hydrogen chloride. The title product (0.68 g) was collected by filtration and recrystallised from propan-2-ol. m.p. 283°-284° (d) (Found: C, 54.3; H, 9.1; Cl, 29.2; N, 5.7. $C_{11}H_{21}Cl_2N.O.25H_2O$ requires C, 54.3; H, 8.9; Cl, 29.2; N, 5.8%).

EXAMPLES 42-50

Preparation of 1-(2-methyl)alkylamino-7,7-dimethylnorbornanes

Method A

1-(2-Methylamino-n-propyl)-7,7-dimethylnorbornane

A mixture of 7,7-dimethyl-1-(2-oxo-n-propyl) norbornane (4.69 g), glacial acetic acid (10 ml), methylamine (10g) and ethanol (100 ml) was heated under reflux for 1 hour, cooled to room temperature and hydrogenated for 4 hours at 4 atmospheres using platinum oxide (0.25 g) as catalyst. The catalyst was removed by filtration and the filtrate evaporated to low volume before extracting with ether. The aqueous phase was basified with 2N-sodium hydroxide solution and the liberated base extracted into ether. The combined extracts were washed with water, dried ($MgSO_4$) and evaporated in vacuo to yield the title product (4.15 g) which was characterised as the hydrochloride salt.

Method B

A solution of the appropriate amine (1.25 equivs.) or amine hydrochloride (1.25 equivs.) in methanol was adjusted to pH 7–8 using 5N-methanolic hydrogen chloride solution or potassium hydroxide respectively. To this solution was added 7,7-dimethyl-1-(2-oxo-n-propyl) norbornane (1 equiv., or its 2-chloro derivative where appropriate) and the resulting mixture stirred for 0.25 hours. A solution of sodium cyanoborohydride (2 equivs.) in methanol was added and the reaction mixture stirred for a length of time depending upon the amine used. The mixture was then basified with potassium hydroxide and extracted with ether. The combined extracts were washed with 2N-hydrochloric acid and the combined washings basified with 2N-sodium hydroxide solution. The liberated base was re-extracted into ether, washed with water, dried ($MgSO_4$) and evaporated to yield the free base which was converted to the hydrochloride salt.

Method C

Alternative preparation of 1-(2-dimethylamino-n-propyl)-7,7-dimethylnorbornane hydrochloride A mixture of 1-(2-methylamino-n-propyl)-7,7-dimethylnorbornane (2.93 g), 37% aqueous formaldehyde solution (3.75 ml) and 98% formic acid (2.1 ml) was heated on a steam-bath for 23 hours, cooled, and poured into water (100 ml). The mixture was basified with 2N-sodium hydroxide solution and extracted with ether. The combined extracts were washed with water, dried ($MgSO_4$) and evaporated to an oil (2.93 g).

A solution of hydrogen chloride in ether was added to an ice-cold solution of the free base in ether (50 ml) and the title product filtered. The crude material was recrystallised from ethyl acetate. Yield: 2.24 g.

These experiments and the products are summarised in Table 3 below.

EXAMPLE 51

1-(3-Amino-2-hydroxy)-n-propyl-2-endo-chloro-7,7-dimethylnorbornane hydrochloride A solution of 2-endo-chloro-1-(3-diazo-2-oxo)propyl-7,7-dimethylnorbornane (4.81g) in dry tetrahydrofuran (60 ml) was added to a stirred suspension of lithium aluminium hydride (1.9g) in tetrahydrofuran (30 ml) over 0.3 hr. The resulting mixture was then stirred at room temperature for 0.25 hr. and cooled in an ice-bath. Water (5 ml) and 2N-sodium hydroxide (10 ml) were added and the mixture stirred at room temperature for 0.5 hr before filtering through Kieselguhr. The filtrate was evaporated to low volume, partitioned between ether and water and the ether layer separated. The aqueous solution was extracted with a further portion of ether and the extracts combined. After washing with water the ethereal solution was extracted with 2N-hydrochloric acid and the combined acid solution basified with 2N-sodium hydroxide. The liberated free base was extracted with ether, washed with water and dried ($MgSO_4$). Evaporation of the solvent yielded the free base which was converted to the title hydrochloride (0.589g) m.p. 176°–179° (d) (from propan-2-ol) (Found: C, 53.8; H, 8.7; Cl, 26.1; N, 5.6. $C_{12}H_{22}ClNO.HCl$ requires C, 53.7; H, 8.6; Cl, 26.4; N, 5.2%).

EXAMPLE 52

1-(3-Amino-2-hydroxy)-n-propyl-7,7-dimethylnorbornane hydrochloride

Using the method described in Example 40, 1-(3-diazo-2-oxo)-n-propyl-7,7-dimethylnorbornane (10.31 g) yielded the title compound (0.67 g), m.p. 268° (d) (from absolute ethanol/ether). (Found: C, 61.5; H, 10.5; Cl, 15.0; N, 5.95. $C_{12}H_{24}ClNO$ requires C, 61.65; H, 10.35; Cl, 15.2; N, 6.0%).

TABLE 3

1-(2-Methyl)Alkylamino-7,7-Dimethylnorbornanes

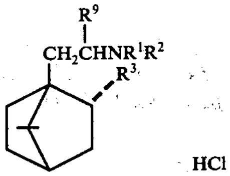

| Ex. No. | $R^9$ | $-NR^1R^2$ | HCl $R^3$ | Method Of Prepn. | m.p. °C | Recrystallisation Solvent | Empirical Formula | C Found | C Req. | H Found | H Req. | Cl Found | Cl Req. | N Found | N Req. |
|---|---|---|---|---|---|---|---|---|---|---|---|---|---|---|---|
| 42 | $CH_3$ | $NH_2$ | H | B | > 250 | Propan-2-ol | $C_{12}H_{24}Cl\ N$ | 66.25 | 66.2 | 11.1 | 11.1 | 16.4 | 16.3 | 6.1 | 6.4 |
| 43 | $CH_3$ | $NHCH_3$ | H | A | 208–210 | Ethanol/Ether | $C_{13}H_{26}Cl\ N$ | 67.5 | 67.35 | 11.5 | 11.3 | 15.0 | 15.3 | 5.9 | 6.0 |
| 44 | $CH_3$ | $N(CH_3)_2$ | H | B,C | 155–7 | Ethyl Acetate | $C_{14}H_{28}Cl\ N$ 0.75 $H_2O$ | 64.9 | 64.8 | 11.5 | 11.5 | 14.2 | 13.7 | 5.3 | 5.4 |
| 45 | $CH_3$ | P | H | B | 223–6 (d) | Ethyl Acetate | $C_{17}H_{32}Cl\ N$ | 71.3 | 71.4 | 11.2 | 11.3 | 12.3 | 12.4 | 4.7 | 4.9 |
| 46 | $CH_3$ | $NH_2$ | Cl | B | 197–9 | Ethanol/Ether | $C_{12}H_{23}Cl_2N$ 0.25 $H_2O$ | 56.1 | 56.1 | 9.0 | 9.2 | 28.1 | 27.6 | 5.7 | 5.5 |
| 47 | $CH_3$ | $N(CH_3)_2$ | Cl | B | 167–170 | Ethyl Acetate | $C_{14}H_{27}Cl_2N$ | 60.2 | 60.0 | 9.9 | 9.7 | 25.2 | 25.3 | 4.7 | 5.0 |
| 48 | $CH_3$ | Py | Cl | B | 166–8 | Ethyl Acetate | $C_{16}H_{29}Cl_2N$ | 63.0 | 62.7 | 9.7 | 9.5 | 23.2 | 23.15 | 4.5 | 4.6 |
| 49 | $CH_3$ | P | Cl | B | 168–171 | Ethyl Acetate | $C_{17}H_{31}Cl_2N$ | 63.3 | 63.7 | 9.7 | 9.8 | 21.6 | 22.1 | 4.4 | 4.4 |
| 50 | $CH_3$ | Py | H | B | 193–5 | Ethyl Acetate | $C_{16}H_{30}Cl\ N$ | 70.4 | 70.7 | 11.1 | 11.1 | 13.45 | 13.0 | 4.9 | 5.15 |

d = decomposition;
p = piperidino;
Py = pyrrolidino

EXAMPLE 53

Alternative preparation of 1-(3-Amino-n-propyl)-2-endo chloro-7,7-dimethylnorbornane hydrochloride (1) 2-endo-Chloro-1-apocamphane-β-ethyl methane sulphonate A solution of methane sulphonyl chloride (0.43 ml) in methylene chloride (5 ml) was added over 10 min. to a stirred solution of 2-endo-chloro-1-apocamphane-62-ethanol (1 g) and triethylamine (1 ml) in methylene chloride (20 ml) at 0°. After 30 min. the reaction mixture was washed successively with iced-water, cold N-hydrochloric acid solution, saturated sodium hydrogen carbonate solution and brine. The organic layer was dried ($MgSO_4$) and evaporated under reduced pressure. The residue (1.28 g) was purified by preparative layer chromatography to give the title compound as an oil (1.1 g), (Found: C, 51.7; H, 7.6; Cl, 12.4; S, 11.4. $C_{12}H_{21}ClO_3S$ requires C, 51.3; H, 7.5; Cl, 12.6; S, 11.4%).

(2) 2-endo-Chloro-1-(2-cyanoethyl)-7,7-dimethylnorbornane

A mixture of 2-endo chloro-1-apocamphane-β-ethyl methane sulphonate (0.9 g), sodium cyanide (0.45 g) and dimethylformamide (8 ml) was stirred at 50°-60° for 4 h. The reaction mixture was then cooled and partitioned between ether and water. The organic layer was washed with water, dried ($MgSO_4$) and evaporated under reduced pressure. The residue (0.74 g) was purified by preparative layer chromatography to give the title compound as an oil (0.57 g). (Found: C, 68.1; H, 8.55; Cl, 16.7; N, 6.6. $C_{12}H_{18}ClN$ requires C, 68.1; H, 8.6; Cl, 16.75; N, 6.6%).

(3) 1-(3-Amino-n-propyl)-2-endo chloro-7,7-dimethylnorbornane hydrochloride

A solution of 2-endo chloro-1-(2-cyano-ethyl)-7,7-dimethylnorbornane (0.5 g) in anhydrous ether (15 ml) was added slowly to a stirred suspension of lithium aluminium hydride (0.5 g) in ether (15 ml). The mixture was stirred at room temperature for 1.5 h. and then cooled in ice. Water was added cautiously and the suspension was filtered. The filtrate was washed with water, dried ($MgSO_4$) and evaporated under reduced pressure. The residue (0.46 g) in ether (15 ml) was treated with a slight excess of an 8N-ethanolic hydrogen chloride solution and the salt (0.38 g) was collected by filtration. Crystallisation from ethanol/ether gave the title compound (0.34 g, 57%), m.p. 248° decomp.).

EXAMPLE 54

| 1. Tablet containing 40 mg active ingredient (per tablet) | |
|---|---|
| Active ingredient | 40.0 mg |
| Lactose | 201.5 mg |
| Maize Starch (dry) | 45.0 mg |
| Aerosil 200 | 6.0 mg |
| Polyvinylpyrrolidone (p.v.p) | 6.0 mg |
| Magnesium stearate | 1.5 mg |
| Tablet weight: | 300.0 mg |

The compound is screened 100 mesh, blended with lactose starch and Aerosil and re-screened through 60 mesh. The p.v.p. is dissolved in I.M.S. and used to granulate the powder blend. The wet granulate is passed through 12 mesh and dried before screening 20 mesh, lubricating with magnesium stearate and compressing.

| 2. Alternative formula for tablet containing 500 mg active ingredient | |
|---|---|
| Active ingredient | 500.0 mg |
| Icing Sugar | 82.0 mg |
| Polyvinylpyrrolidone (p.v.p) | 12.0 mg |
| Magnesium Stearate | 6.0 mg |
| Tablet weight: | 600.0 mg |

Tablets are prepared as for (1) i.e. the powder blend is granulated with an I.M.S. solution of p.v.p.

The preparation of certain intermediates required in the above examples is described below.

PREPARATION 1

Ethyl apocamphaneacetate

Apocamphaneacetic acid (9.13 g) and thionyl chloride (10 ml) were heated on a steam-bath for 1 hour and evaporated in vacuo. Absolute ethanol (6ml) was added, over 0.25 hours, to a cooled, stirred solution of the residue in sodium dried ether (25 ml). The solution was then stirred at room temperature for 1.5 hours and poured into water (150 ml). The product was extracted with ether and the combined extracts washed successively with water, dilute sodium bicarbonate solution and water. The ethereal solution was dried ($MgSO_4$) and evaporated in vacuo to yield the title product which was distilled at 65° and 0.3 mm of Hg. Yield: 9.10 g. (Found: C, 73.9; H, 10.7. $C_{13}H_{22}O_2$ requires C, 74.2; H, 10.5%).

PREPARATION 2

Ethyl 2-(7,7-dimethylnorborn-1-yl)propionate

A 2.1M solution (10.5 ml) of butyl lithium in hexane was added dropwise to a stirred solution of N-isopropylcyclohexylamine (3.11 g) in dry tetrahydrofuran (20 ml) cooled at −78° under nitrogen. The resulting pale yellow solution was stirred at −78° for 0.25 hours before ethyl apocamphaneacetate (4.20 g) was added and the mixture stirred at −78° for 0.75 hours. Iodomethane (1.87 ml) was added to the stirred mixture and the temperature maintained at −78° for 0.25 hours before allowing the temperature to rise to −20° over 0.75 hours. The resulting mixture was then acidified with 5N-hydrochloric acid and extracted with ether. The combined extracts were washed several times with water, dried ($MgSO_4$) and evaporated to yield the crude product (4.33 g). The oil was distilled at 60° and 0.2 mm to yield the title compound (2.92 g) as a pale yellow liquid. (Found: C, 75.6; H, 11.2. $C_{14}H_{24}O_2$ requires C, 75.0; H, 10.8%).

PREPARATION 3

2-(7,7-Dimethylnorborn-1-yl)propionic acid

Boron tribromide (38.0 ml) was added dropwise to a stirred solution of ethyl 2-(7,7-dimethylnorborn-1-yl)propionate (22.4 g) in dichloromethane (170 ml), cooled at −78°. When the addition was complete the temperature was maintained at −78° for 1 hour and then allowed to attain room temperature and stirred overnight. The mixture was then poured onto ice/water (1 l.) and extracted with dichloromethane. The combined extracts were washed with water, dried ($MgSO_4$), and evaporated in vacuo to yield an oil (20.66 g).

A solution of the oil in ether was extracted several times with 2N-sodium hydroxide. The remaining ethereal solution was washed with water, dried ($MgSO_4$) and evaporated in vacuo to an oil (15.01 g) which was identified (by infrared and nuclear magnetic resonance spectra) as 2-(7,7-dimethylnorborn-1-yl)propionic anhydride. The alkaline extracts were acidified with 2N-hydrochloric acid and the free acid extracted into ether. The combined extracts were washed with water, dried ($MgSO_4$) and evaporated in vacuo to yield the title compound (4.80 g) as a cream coloured solid, m.p. 93°-95° [from light-petroleum (b.p. 40°-60°)] (Found: C, 73.6; H, 10.25. $C_{12}H_{20}O_2$ requires C, 73.4; H, 10.3%).

A mixture of the above anhydride (14.72 g) and 2N-sodium hydroxide (59 ml) was stirred and heated at 100° for 2 hours and cooled. The cooled solution was extracted with ether and the extracts discarded. The remaining alkaline solution was acidified with 5N-hydrochloric acid and extracted with ether. The extracts were combined, washed with water, dried ($MgSO_4$) and evaporated in vacuo to yield the title compound (12.36 g), identical with an authentic sample.

PREPARATION 4

7,7-Dimethyl-1-(2-oxo-n-propyl)norbornane

A solution of 1-apocamphaneacetic acid (9.12 g) in sodium dried ether (50 ml) was cooled in an ice-bath and stirred under nitrogen whilst a 1.9M solution (58 ml) of methyl lithium was added dropwise. When the addition was complete the mixture was heated under reflux for 2 hours, cooled in an ice-bath and acidified with 2N-hydrochloric acid. After stirring for 0.5 hours the mixture was extracted with ether and the combined extracts washed with water, dilute sodium bicarbonate and finally with water. The ethereal solution was dried ($MgSO_4$), evaporated in vacuo and the residual oil distilled at 0.1 mm. The fraction boiling at 44.5°-47°, the title product, was collected. Yield: 5.1 g. (Found: C, 80.3; H, 11.3. $C_{12}H_{20}O$ requires C, 79.9; H, 11.3%)

PREPARATION 5

1-(2-Bromoethyl)-7,7-dimethylnorbornane

A stirred mixture of 1-(2-hydroxyethyl)-7,7-dimethylnorbornane (42.0 g, 0.25 mole), 48% hydrobromic acid (63.0 ml) and concentrated sulphuric acid (14 ml) was heated under reflux for 4 hours, cooled, poured into water (500 ml) was extracted with ether. The combined extracts were washed with water, sodium bicarbonate solution and water. After drying ($MgSO_4$) the solvent was evaporated in vacuo to yield the title product (50.9 g), m.p. 68°-71° [from light-petroleum (b.p. 40-60°)] (Found: C, 57.0: H, 8.1; Br, 34.2. $C_{11}H_{19}Br$ requires C, 57.0; H, 8.3; Br, 34.5%).

PREPARATIONS 6-36

Preparation of 7,7-dimethylnorborn-1-yl alkylcarbonamides

The amides whose properties are summarised in Table 4 were prepared by one or both of the following methods.

The appropriate carboxylic acid and excess thionyl chloride were heated on a steam-bath for 1 hour and evaporated to an oil in vacuo. The acid chloride was then used in the following preparations without further purification.

Method A

A solution of the freshly prepared acid chloride in toluene was stirred and cooled in an ice-bath whilst a solution (usually 30% w/v) of the appropriate amine (2.2 equivalents) in toluene was added dropwise. When addition was complete the mixture was allowed to come to room temperature and filtered. The filtrate was evaporated, dissolved in ether, washed with 2N-hydrochloric acid, water, dilute sodium bicarbonate, water and dried over magnesium sulphate. Evaporation of the organic solvent afforded the crude amide which was purified by preparative thin-layer chromatography and/or crystallization.

METHOD B

A solution of the appropriate acid chloride in dry ether was added dropwise with stirring to an ice-cold solution of diazomethane (approximately 2 equivalents) in ether; the mixture was stirred at 0° for 1 hour and then left at room temperature overnight. Removal of the solvent in vacuo gave a yellow oil which was used without further purification.

A mixture of concentrated ammonia (d, 0.880) (15 ml) and 10% silver nitrate solution (12 ml) was added to a stirred solution of the crude diazoketone [1-(3-diazo-2-oxo)-n-propyl-7,7-dimethylnorbornane] (5.16g) in dioxan (25 ml) at 70°. When evolution of gas had ceased (0.75 hours), further ammonia solution (15 ml) was added and the stirred mixture heated to 90°-100° for 2 hours. The mixture was allowed to stand overnight at room temperature and then filtered. The filtrate was extracted with ether and the combined extracts washed with water, dilute hydrochloric acid, water, dilute sodium bicarbonate solution and water. After drying ($MgSO_4$) the solvent was evaporated in vacuo to yield 1-(3-amino-3-oxo)-n-propyl-7,7-dimethylnorbornane (3.80g).

Other amides indicated in Table 4 were prepared using the above procedure.

Method A was used in Preparations 6-21 and 25-36 and method B was additionally used as an alternative method in Preparations 18 and 20. Method B was used in Preparations 22-24.

TABLE 4

7,7-DIMETHYLNORBORN-1-YL ALKYLCARBONAMIDES

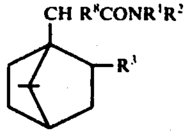

| PREP. NO. | $NR^1R^2$ | $R^3$ | m.p. °C | RECRYSTALLISATION SOLVENT | EMPIRICAL FORMULA | C FOUND | C REQ. | H FOUND | H REQ. | Cl FOUND | Cl REQ. | N FOUND | N REQ. |
|---|---|---|---|---|---|---|---|---|---|---|---|---|---|
| 6 | $NH_2$ | H | 137-8 | LIGHT-PETROLEUM (b.p. 80-100°) | $C_{11}H_{19}NO$ | 72.8 | 72.9 | 10.8 | 10.6 | | | 7.6 | 7.7 |
| 7 | $NH_2$ | Cl | 103-5 | LIGHT-PETROLEUM (b.p. 60-80°) | $C_{11}H_{18}Cl\ NO$ | 61.2 | 61.2 | 8.5 | 8.4 | 16.5 | 16.4 | 6.4 | 6.5 |
| 8 | NHMe | H | 119-121 | LIGHT PETROLEUM (b.p. 60-80°) | $C_{12}H_{21}NO$ | 73.7 | 73.8 | 10.8 | 10.8 | | | 6.8 | 7.2 |
| 9 | NHMe | Cl | 129-130 | ETHYL ACETATE/ LIGHT-PETROLEUM (b.p. 80-100°) | $C_{12}H_{20}Cl\ NO$ | 62.7 | 62.7 | 8.8 | 8.8 | 15.3 | 15.4 | 6.1 | 6.1 |
| 10 | $NMe_2$ | H | | (b) | $C_{13}H_{23}NO$ 0.1 $CH_3COOC_2H_5$ | 73.8 | 73.7 | 11.1 | 11.0 | | | 6.4 | 6.2 |
| 11 | $NMe_2$ | Cl | | (b) | $C_{13}H_{22}Cl\ NO$ | 64.2 | 64.05 | 9.1 | 9.1 | 14.1 | 14.55 | 5.4 | 5.7 |
| 12 | P | H | | (b) | $C_{16}H_{27}NO$ | 77.2 | 77.1 | 10.8 | 10.9 | | | 5.65 | 5.6 |
| 13 | P | Cl | | (b) | $C_{16}H_{26}Cl\ NO$ | 67.3 | 67.7 | 9.2 | 9.2 | 12.0 | 12.5 | 4.6 | 4.9 |
| 14c | $NMe_2$ | H | 45-6 | (b) | $C_{14}H_{25}NO$ | 75.6 | 75.3 | 11.0 | 11.3 | | | 6.0 | 6.3 |
| 15c | P | H | | (b) | $C_{17}H_{29}NO$ | 78.3 | 77.5 | 11.2 | 11.1 | | | 4.9 | 5.3 |
| 16 | 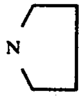 | H | 54-5 | PENTANE | $C_{15}H_{25}NO$ | 76.4 | 76.5 | 10.6 | 10.7 | | | 5.5 | 5.95 |
| 17 | 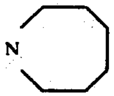 | Cl | | b | $C_{17}H_{28}Cl\ NO$ | 68.3 | 68.55 | 9.4 | 9.5 | 11.8 | 11.9 | 4.4 | 4.7 |

(c): In Preparations 14 and 15, the group at the 10-position is $-\overset{\overset{CH_3}{|}}{C}H-$ (i.e. $R^8 = CH_3$); in Preparations 6-13 and 16 and 17 $R^8$ is H (b) Purified by prep. t.l.c.

P =

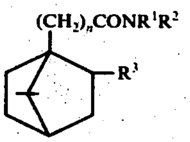

| PREP NO. | n | $NR^1R^2$ | $R^3$ | m.p. °C | RECRYSTALLISATION SOLVENT | EMPIRICAL FORMULA | C FOUND | C REQ. | H FOUND | H REQ. | N FOUND | N REQ. |
|---|---|---|---|---|---|---|---|---|---|---|---|---|
| 18 | 2 | $NH_2$ | H | 143-5 | LIGHT-PETROLEUM (b.p. 100-120°) | $C_{12}H_{21}NO$ | 73.9 | 73.4 | 10.9 | 10.8 | 7.0 | 7.2 |
| 19 | 2 | NHMe | H | 85-6 | LIGHT-PETROLEUM (b.p. 60-80°) | $C_{13}H_{23}NO$ | 74.6 | 74.6 | 11.2 | 11.0 | 6.8 | 6.7 |
| 20 | 2 | $NMe_2$ | H | 62-4 | LIGHT PETROLEUM (b.p. 40-60°) | $C_{14}H_{25}NO$ | 75.4 | 75.3 | 11.6 | 11.3 | 6.1 | 6.3 |

TABLE 4-continued

| PREP NO. | n | $NR^1R^2$ | $R^3$ | m.p. °C | RECRYSTALLISATION SOLVENT | EMPIRICAL FORMULA | C FOUND | C REQ. | H FOUND | H REQ. | Cl FOUND | Cl REQ. | N FOUND | N REQ. |
|---|---|---|---|---|---|---|---|---|---|---|---|---|---|---|
| 21 | 2 | P | H | 53-4 | ETHYL ACETATE/ LIGHT-PETROLEUM (b.p. 60-80°) | $C_{17}H_{29}NO$ | 77.5 | 77.5 | 11.1 | 11.1 | | | 5.1 | 5.3 |

7,7-DIMETHYLNORBORN-1-YL ALKYLCARBONAMIDES

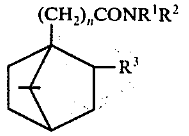

| PREP NO. | n | $NR^1R^2$ | $R^3$ | m.p. °C | RECRYSTALLISATION SOLVENT | EMPIRICAL FORMULA | C FOUND | C REQ. | H FOUND | H REQ. | Cl FOUND | Cl REQ. | N FOUND | N REQ. |
|---|---|---|---|---|---|---|---|---|---|---|---|---|---|---|
| 22 | 2 | NHMe | Cl | | (b) | $C_{13}H_{22}ClNO$ | 64.5 | 64.05 | 9.25 | 9.1 | 13.8 | 14.55 | 5.2 | 5.75 |
| 23 | 2 | $NMe_2$ | Cl | | (b) | $C_{14}H_{24}ClNO$ 0.25$H_2O$ | 63.9 | 64.1 | 9.5 | 9.4 | 14.0 | 13.5 | 4.9 | 5.3 |
| 24 | 2 | P | Cl | | (b) | $C_{17}H_{28}ClNO$ | 69.0 | 68.5 | 9.5 | 9.5 | 12.0 | 11.9 | 4.3 | 4.7 |
| 25 | 3 | $NH_2$ | H | 133-135.5 | LIGHT-PETROLEUM (b.p. 80-100) | $C_{13}H_{23}NO$ | 74.7 | 74.6 | 11.2 | 11.1 | | | 6.4 | 6.7 |
| 26 | 3 | NHMe | H | | (b) | $C_{14}H_{25}NO$ | 75.1 | 75.3 | 11.3 | 11.3 | | | 6.2 | 6.3 |
| 27 | 3 | $NMe_2$ | H | | (b) | $C_{15}H_{27}NO$ 0.25$CH_3COOC_2H_5$ | 74.8 | 74.1 | 11.2 | 11.3 | | | 5.4 | 5.4 |
| 28 | 3 | P | H | | (b) | $C_{18}H_{31}NO$ | 77.7 | 77.9 | 11.0 | 11.3 | | | 5.1 | 5.05 |
| 29 | 3 | $NMe_2$ | Cl | | (b) | $C_{15}H_{26}ClNO$ | | | | | | | | |
| 30 | 3 | P | Cl | | (b) | $C_{18}H_{30}ClNO$ | | | | | | | | |
| 31 | 1 | $NEt_2$ | Cl | | (b) | $C_{15}H_{26}ClNO$ | 66.6 | 66.3 | 9.6 | 9.6 | 12.8 | 13.0 | 5.3 | 5.15 |
| 32 | 1 | 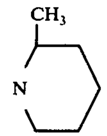 | Cl | | (b) | $C_{17}H_{28}ClNO$ | | | | | | | | |
| 33 | 1 | 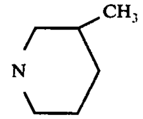 | Cl | | (b) | $C_{17}H_{28}ClNO$ | 68.6 | 68.55 | 9.45 | 9.5 | 12.2 | 11.9 | 4.6 | 4.7 |
| 34 | 1 | 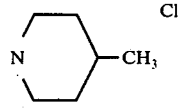 | Cl | | (b) | $C_{17}H_{28}ClNO$ | 68.2 | 68.55 | 9.35 | 9.5 | 12.1 | 11.9 | 4.5 | 4.7 |

TABLE 4-continued
7,7-DIMETHYLNORBORN-1-YL ALKYLCARBONAMIDES
| PREP. NO. | n | NR¹R² | R³ | m.p. ° C | RECRYSTALLISATION SOLVENT | EMPIRICAL FORMULA | C FOUND | C REQ. | H FOUND | H REQ. | Cl FOUND | Cl REQ. | N FOUND | N REQ. |
|---|---|---|---|---|---|---|---|---|---|---|---|---|---|---|
| 35 | 1 | 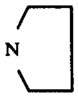 | Cl | 109-112 | LIGHT PETROLEUM (b.p. 60-80)° | $C_{15}H_{24}Cl\ NO$ | 66.35 | 66.8 | 9.1 | 9.0 | 13.1 | 13.1 | 5.0 | 5.2 |
| 36 | 1 | 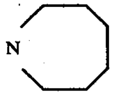 | H | | (b) | $C_{17}H_{29}NO$ | 77.4 | 77.5 | 10.8 | 11.1 | | | 5.1 | 5.3 |

PREPARATION 37

3-(7,7-Dimethylnorborn-1-yl)propionic acid

METHOD A

A solution of 1-(2-bromoethyl)-7,7-dimethylnorbornane (4.623g). in dry ether (20 ml) was added to magnesium turnings (0.534g) and a crystal of iodine. The reaction mixture was stirred and addition of the bromo compound was made at such a rate as to maintain gentle reflux. When the addition was complete the mixture was stirred and heated under reflux for 0.5 hours and cooled. Carbon dioxide was passed through the stirred mixture for 0.5 hours and the resulting mixture poured onto excess solid carbon dioxide. The excess carbon dioxide was allowed to evaporate and the mixture acidified with 5N-hydrochloric acid to yield the title product (0.89g) m.p. 123°–125° (from n-pentane) (Found: C, 73.2; H, 10.45. $C_{12}H_{20}O_2$ requires C, 73.4; H, 10.3%).

Method B

A mixture of 1-(2-bromoethyl)-7,7-dimethylnorbornane (11.56g), I.M.S. (40 ml) and potassium cyanide (7.2 g) was stirred and heated under reflux for 47 hours. Potassium hydroxide (16.84g) was added and the stirred mixture heated under reflux for a further 6 hours. After standing at room temperature overnight the mixture was added to hot water (200 ml), cooled, and extracted with ether. The remaining aqueous phase was cooled in an ice-bath and acidified with concentrated hydrochloric acid. The title product (5.96g) was filtered and dried.

PREPARATION 38

4-(7,7-Dimethylnorborn-1-yl)butyric acid

Sodium metal (3.79g) was dissolved in absolute ethanol (75 ml) and redistilled diethyl malonate (24.00g) was added dropwise, followed by 1-(2-bromoethyl)-7,7-dimethylnorbornane (23.20g). After stirring and heating the mixture under reflux for 2.5 hr. most of the ethanol was distilled and a solution of potassium hydroxide (33.0g) in water (50 ml) was added to the residue. The resulting solution was stirred and heated under reflux for 1.25 hr. and more ethanol removed by distillation. The resulting mixture was cooled, acidified with 50% sulphuric acid and extracted several times with ether. The solid residue from evaporation of the dried ($MgSO_4$) ether extracts was heated in an oil bath at 170°–180° for 0.75 hr. The residue was cooled, taken up in ether and extracted with 2N-sodium hydroxide. The alkaline extracts were acidified with 5N-hydrochloric acid and the liberated acid extracted with ether, washed with water and dried ($MgSO_4$). Evaporation of the ether in vacuo yielded the title product (14.15g). A small amount of the product was purified by preparative thin-layer chromatography yielding a white solid, m.p. 72°–73° (Found: C, 74.15; H, 10.5. $C_{13}H_{22}O_2$ requires C, 74.2; H, 10.5%).

The bulk of the material was used without purification.

PREPARATION 39

1-(2-Chloroethyl)-2-endo-chloro-7,7-dimethylnorbornane

Thionyl chloride (9.52g) was added dropwise to a stirred solution of 2-endo-chloro-1-(2-hydroxyethyl)-7,7-dimethylnorbornane (8.1g) in dry pyridine (3.16g) and the resulting mixture heated under reflux for 0.75 hr. After allowing to cool to room temperature the reaction mixture was poured into ice/water (100 ml) and stirred for 0.75 hr. The mixture was extracted with ether and the combined extracts washed with water, dilute sodium bicarbonate solution and finally with water. After drying ($MgSO_4$) and evaporating the solvent, the title product was distilled. Yield, 7.20g. b.p. 102°–108° at 1.2 mm. of Hg. (Found: C, 59.7; H, 7.9; Cl, 31.6; $C_{11}H_{18}Cl_2$ requires C, 59.7; H, 8.2; Cl, 32.1%).

PREPARATION 40

4-(2-endo-Chloro-7,7-dimethylnorborn-1yl)-butyric acid

By a similar procedure to Preparation 38, 1-(2-chloroethyl)-2-endo-chloro-7,7-dimethylnorbornane (21.4 g) yielded title product (12.64 g) which was used without further purification.

A small portion was purified by preparative tlc and recrystallisation from n-pentane. m.p. 51°–53° (Found C, 65.2; H, 8.9; Cl, 12.9. $C_{13}H_{21}ClO_2.0.25C_5H_{12}$ requires C, 65.1; H, 9.2; Cl, 13.5%).

PREPARATION 41

2-endo-Chloro-1-(3-diazo-2-oxo)propyl-7,7-dimethylnorbonnane 2-endo-Chloro-1-apocamphaneacetic acid (10.85g) and excess thionyl chloride were heated on a steam-bath for 1 hr. and evaporated to an oil under reduced pressure.

A solution of the oil in dry ether was added dropwise with stirring at 0° to an ethereal solution of diazomethane (ca. 2 equiv.). The solution was stirred at 0° for 1 hr. and then left at room temperature overnight. Removal of the solvent in vacuo yielded the title product (12.0g) which was used without further purification.

PREPARATION 42

2-endo-Chloro-7,7-dimethyl-1-(2-oxo-n-propyl)norbonane

Using the method of Preparation 4, with 2-endo-chloro-1-apocamphaneacetic acid (10.84g) as the starting material, the residual oil was distilled at 0.25 mm, and the fraction collected at 80°–85° was redistilled at 82°–85° and 0.3 mm to yield the title product (6.17 g).

We claim:

1. 7,7-Dimethyl-[2.2.1]-bicycloheptane of the formula:

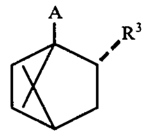

I wherein

A is $-(CH_2)_nNR^1R^2$ wherein n is 2, 3 or 4;

$R^1$ and $R^2$, which may be the same or different, are hydrogren atoms or $C_{1-6}$ alkyl or $C_{2-6}$ alkenyl groups or, together with the intervening nitrogen atom, represent a 4–7 membered saturated heterocylic ring which is unsubstituted or substituted by a $C_{1-6}$ alkyl group; and $R^3$ is a chlorine atom in the endo configuration; which compounds may optionally be substituted by a $C_{1-4}$ alkyl group at any position on the alkylene chain of A, or by an oxo or hydroxy group at the $\beta$-position of the alkylene chain of A relative to the nitrogen atom;

or the physiologically acceptable acid addition salts thereof.

2. A compound as claimed in claim 1 wherein the acid addition salt is selected from the group consisting of the hydrochlorides, hydrobromides, phosphates, sulphates, p-toluene sulphonates, methane sulphonates, citrates, tartrates, acetates, ascorbates, lactates, maleates and succinates.

3. Compounds as claimed in claim 1 wherein the alkylene chain of A is unsubstituted.

4. A compound as claimed in claim 1 wherein $R^1$ and $R^2$ are both hydrogen atoms.

5. A compound as claimed in claim 1 wherein $-NR^1R^2$ is a methylamino group.

6. A compound as claimed in claim wherein n is 2.

7. A compound as claimed in claim 1 wherein n is 3.

8. A compound as claimed in claim 1 wherein n is 4.

9. A compound as claimed in claim 1 wherein said compound is 1-(2-aminoethyl)-2-endo-chloro-7,7-dimethylnorbornane, 1-(2-dimethylaminoethyl)-2-endo-chloro-7,7-dimethylnorbornane, 1-(2-piperidinoethyl)-2-endo-chloro-7,7-dimethylnorbornane, or the salts thereof.

10. A compound as claimed in claim 1, said compounds being 1-(3-amino-n-propyl)-2-endo-chloro-7,7-dimethylnorbornane, 1-(3-methylamino-n-propyl)-2-endo-chloro-7,7-dimethyl-norbornane, 1-(3-dimethylamino-n-propyl)-2-endo-chloro-7,7-dimethyl-norbornane, 1-(2-oxo-3-methylamino-n-propyl)-2-endo-chloro-7,7-dimethyl-norbornane, 1-(2-hydroxy-3-amino-n-propyl)-2-endo-chloro-7,7-dimethylnorbornane, or the salts thereof.

11. A compound as claimed in claim 1 wherein said compound is 1-(2-pyrrolidinoethyl)-2-endo-chloro-7,7-dimethylnorbornane, 1-(2-amino-n-propyl)-2-endo-chloro-7,7-dimethylnorbornane, or the salts thereof.

12. The compound 1-(3-amino-n-propyl)-2-endo-chloro-7,7-dimethylnorbornane; and its physiologically acceptable acid addition salts.

13. A pharmaceutical composition for treating Parkinsons disease comprising an effective anti-Parkinsonism amount of a compound as claimed in claim 1 or a physiologically acceptable salt thereof together with a pharmaceutical carrier or excipient.

14. A pharmaceutical composition for treating anxiety comprising a tranquilizing effective amount of a compound as claimed in claim 1 or a physiologically acceptable salt thereof, together with a pharmaceutical carrier or excipient.

15. A method of treating Parkinson's disease which comprises administering to a patient or animal in need of such treatment an effective anti-Parkinsonism amount of a compound as claimed in claim 1.

16. The method of treating Parkinson's disease as claimed in claim 15 wherein the compound is 1-(3-amino-n-propyl)-2-endo-chloro-7,7-dimethylnorbornane; or its physiologically acceptable acid addition salts.

17. A method of treating anxiety which comprises administering to a patient in need of such treatment an effective tranquilizing amount of a compound as claimed in claim 1.

* * * * *